US006884078B2

(12) United States Patent
Wiig et al.

(10) Patent No.: US 6,884,078 B2
(45) Date of Patent: Apr. 26, 2005

(54) TEST OF PARIETAL LOBE FUNCTION AND ASSOCIATED METHODS

(75) Inventors: Elisabeth Wiig, Arlington, TX (US); Niels Peter Nielsen, Kobenhavn (DK); Lennart Minthon, Lund (SE); Siegbert Warkentin, Limhamn (SE)

(73) Assignee: Harcourt Assessment, Inc., San Antonio, TX (US)

( * ) Notice: Subject to any disclaimer, the term of this patent is extended or adjusted under 35 U.S.C. 154(b) by 0 days.

(21) Appl. No.: 10/245,456

(22) Filed: Sep. 17, 2002

(65) Prior Publication Data

US 2004/0058306 A1 Mar. 25, 2004

(51) Int. Cl.[7] .............................................. G09B 19/00
(52) U.S. Cl. ....................... 434/236; 434/322; 434/323; 434/362
(58) Field of Search ................................ 434/236, 362, 434/333, 354

(56) References Cited

U.S. PATENT DOCUMENTS

| | | | | |
|---|---|---|---|---|
| 6,159,014 A | * | 12/2000 | Jenkins et al. .............. | 434/169 |
| 6,364,845 B1 | * | 4/2002 | Duffy et al. ................. | 600/558 |
| 6,435,878 B1 | * | 8/2002 | Reynolds et al. ........... | 434/236 |
| 6,497,576 B1 | * | 12/2002 | Smith .......................... | 434/236 |

OTHER PUBLICATIONS

Mindstreams Computerized Cognitive Tests, NeuroTrax Corp, 1999–2003, pp. 1–3.*
Wiig et al., "Parietal Lobe Activation in Rapid, Automatized Naming by Adults," Perceptual and Motor Skills, 94, pp. 1230–1244, 2002.
Leung et al., "An Event–Related Functional MRI Study of the Stroop Color Word Interference Task," Cerebral Cortex 10(6), 552–560, 2000.

(Continued)

*Primary Examiner*—Derris H. Banks
*Assistant Examiner*—John Sotomayor
(74) *Attorney, Agent, or Firm*—Allen, Dyer, Doppelt, Milbrath & Gilchrist, P.A.

(57) ABSTRACT

A test, system, and method for testing parietal lobe function in a subject, wherein the method includes displaying to a subject a first ordered array of objects having a variety of colors, which the subject is prompted to name. The named object colors are compared with the correct object colors, and a count is maintained of errors in the named object colors and an interval taken by the subject to complete naming the object colors, these numbers compared with predetermined data for determining a possible parietal lobe function deficiency. An analogous test is performed of shape-naming, and, in a preferred embodiment, of color and shape naming. A practice test administration is also described, as well as a software-driven administration and scoring of the test.

31 Claims, 18 Drawing Sheets

OTHER PUBLICATIONS

Brown, et al., "On a Variant of Stroop's Paradigm: Which Cognitions Press Your Buttons?," Memory & Cognition, 29(6), 903–904Sep. 2001.

Bondi et al., "Cognitive and Neuropathologic Correlates of Stroop Color–Word Test Performance in Alzheimer's Disease," Neuropsychology 16(3), 335–343, 2002.

Long et al., "Working Memory and Stroop Interference: An Individual Differences Investigation," Memory & Cognition, 30(2), 294–301, 2002.

Early Alert Alzheimers Home Screening Test, online, http://www.testsymptomsathome.com/fmg01.asp, retrieved from the Internet on Aug. 13, 2002.

Boxtel et al., "Visual Determinants of Reduced Performance on the Stroop Color–Word Test in Normal Aging Individuals," Journal of Clinical and Experimental Neuropsychology 23(5), 620–627, 2001.

Milham et al., "The Relative Involvement of Anterior Cingulate and Prefrontal Cortex in Attentional Control Depends on Nature of Conflict," Cognitive Brain Research 12, 467–473, 2001.

Fan et al., "Assessing the Heritability of Attentional Networks," BMC Neuroscience 2(14), pp. 1–7, 2001.

Corina et al., "fMRI Auditory Language Differences Between Dyslexic and Able Reading Children," NeuroReport 12(6), 1195–1201, May 2001.

Swanson et al., "Attention Deficit/Hyperactivity Disorder Children with a 7–Repeat Allele of the Dopamine Receptor D4 Gene have Extreme Behavior but Normal Performance on Critical Neuropsychological Test of Attention," PNAS 97(9), 4754–4759, Apr. 2000.

Wiig et al., "Comparison of Rapid Naming Abilities in Language–Learning–Desabled and Academically Achieving Eight–Year–Olds," Language, Speech, and Hearing Services in the Schools 13(1), 11–23, Jan. 1982.

Rapport et al., "Executive Functioning in Adult Attention-Deficit Hyperactivity Disorder," The Clinical Neuropsychologist 15(4), 479–491 Dec. 2001.

Leverett et al., "Correlations for the Stroop Color and Word Test with Measures of Reading and Language Achievement," Perceptual and Motor Skills 94(1), 459–466, Apr. 2002.

Stroop Color and Word Test 2002, online, http://www-.parinc.com/product.cfm?ProductID=565, retrieved from the Interent on Aug. 13, 2002.

Levy, C.M. and Weilbacher, M.W., "Stroop Effects Version 9.0 for Windows, Instruction Version," online, http://.lifesciassoc.home.pipeline.com/instruct/stroop/strpinst.htm, retrieved from the Internet on Aug. 13, 2002.

Adleman et al., "A Developmental fMRI Study of the Stroop Color–Word Task," NeuroImage 16, pp. 61–75, 2002.

Pujol et al., "The Effect of Medial Frontal and Posterior Parietal Demyelinating Lesions on Stroop Interference," NeuroImage 13, pp. 68–75, 2001.

Fisher et al., "Stroop Color–Word Test: Performance in Patients with Alzheimer's Disease," Journal of Clinical and Experimental Neuropsychology 12(5), 745–758, 1990.

Wiig et al., "A Clinical Rationale for Assessing Rapid Automatized Naming in Children with Language Disorders," Journal of Learning Disabilities 33(4), 359, 2000.

* cited by examiner

Response Form 70

Name _____ Sex ☐M ☐F
Address _____
Daytime Phone _____

| | Year | Month | Day |
|---|---|---|---|
| Date Tested | | | |
| Date of Birth | | | |
| Age | | | |

Examiner _____ Site _____

| Test/Task | Total Naming Time | Types of Naming Errors | | | Time Performance Range | | | Accuracy Performance Range | | |
|---|---|---|---|---|---|---|---|---|---|---|
| | | Self-Corrected | Uncorrected Errors | Total Errors | Normal | Slower-Than-Normal | Non-Normal/Pathological | Normal | More Errors Than Normal | Non-Normal |
| Color | 74 | 71 | 72 | 73 | - | 76 | - | - | 75 | - |
| Form | 80 | 77 | 78 | 79 | - | 82 | - | - | 81 | - |
| Color-Form | 86 | 83 | 84 | 85 | - | 88 | - | - | 87 | - |
| Color | | | | | | | | | | |
| Number | | | | | | | | | | |
| Color-Number | | | | | | | | | | |
| Color | | | | | | | | | | |
| Letter | | | | | | | | | | |
| Color-Letter | | | | | | | | | | |
| Color | | | | | | | | | | |
| Animal | | | | | | | | | | |
| Color-Animal | | | | | | | | | | |
| Color | | | | | | | | | | |
| Object | | | | | | | | | | |
| Color-Object | | | | | | | | | | |

FIG. 7A

TEST OF PARIETAL LOBE FUNCTION AND ASSOCIATED METHODS

BACKGROUND OF THE INVENTION

1. Field of the Invention

The present invention relates to tests of mental function and methods of administering same, and, more particularly, to such tests for Alzheimer's disease.

2. Description of Related Art

It is known to use rapid automatic naming tasks for probing for neurological impairments. The "Stroop Color-Word Test" and color-form tests are known for testing for Alzheimer's disease. The Stroop Color and Word Test is known to be a standard measure in neurophysiological assessment for measuring cognitive processing. In this test the test-taker looks at a sheet of color words printed in black ink, a color page with "X"s printed in color, and a color-word page with words from the first page printed in colors from the second page, with the color and word not matching. The test-taker looks at each sheet and moves down the columns, reading words or naming the ink colors as quickly as possible within a time limit. The Stroop test is also available for administration via computer.

SUMMARY OF THE INVENTION

It is therefore an object of the present invention to provide a verbally based test of parietal lobe function.

It is a further object to provide such a verbally based test for Alzheimer's disease.

It is another object to provide a method of administering a test of parietal lobe function.

It is an additional object to provide such a method of administering a test for Alzheimer's disease.

These and other objects are achieved by the present invention, a test, system, and method for testing parietal lobe function in a subject. The method comprises the steps of displaying to a subject a first ordered array of objects having a variety of colors. Preferably each object has a unitary shape. The subject is prompted to name the object colors sequentially in order. The named object colors are then compared with the correct object colors, and a count is maintained of errors in the named object colors. Also, an interval taken by the subject to complete naming the object colors is timed.

The color-naming error count and interval are then compared with a predetermined color-naming error count and interval. The maintained color-naming error count and/or the timed interval being greater than the predetermined color-naming error count and interval is indicative of a possible parietal lobe function deficiency.

In another portion of the method, a second ordered array of objects having a variety of shapes is displayed to the subject. The subject is prompted to name the object shapes sequentially in order. The named object shapes are compared with the correct object shapes. A count of errors in the named object shapes is maintained, and an interval taken by the subject to complete naming the object shapes is timed.

The shape-naming error count and interval are then compared with a predetermined shape-naming error count and interval. The maintained shape-naming error count and/or the timed interval being greater than the predetermined shape-naming error count and interval is indicative of a possible parietal lobe function deficiency.

The test, system, and method of the present invention provide a rapid, objective, reliable, and sensitive standardized, neurolinguistic screening tool designed to assess: automaticity, speed, and fluency in naming; the ability to perform rapid cognitive shifts between the visual stimuli that form the input and the semantic fields from which the appropriate names must be retrieved; activation of working memory for processing and monitoring naming of familiar visual stimuli; and parietal lobe functioning associated with neurogenic disorders.

The test of the present invention can be used to screen adolescents and adults for parietal lobe dysfunction indicative of mild cognitive impairments, acquired neurogenic disorders of language and communication (aphasia or TBI, late-onset depression, bipolar disorders, epilepsy), or degenerative neurological disorders such as Alzheimer's or Parkinsonism. It can also be used to screen adolescents or adults with suspected or diagnosed language disorders, learning disabilities (LD), attention deficit/hyperactive disorders (AD/HD), and other syndromes associated with parietal lobe dysfunction. The test is a measure of response speed in which individual differences depend on the speed and accuracy (automaticity) of performance.

Although other continuous naming tasks are known in the art, the present invention is distinguished by the following features:

1. The test is designed to allow for administration and interpretation across linguistic codes and cultural domains.
2. The visual stimuli are familiar across many cultures.
3. The test design enables examiners from other cultural-linguistic communities to develop directions for administration and standards for verbal responses that are representative of their language.
4. Examiners can use the test to conduct comparative evaluations of adolescents and adults with monolingual or bilingual backgrounds.

It will be understood by one of skill in the art that the order presented above is not intended as limiting, and that the order of the two portions of the test administration method may be reversed without departing from the spirit of the invention.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 7A illustrates an exemplary Response Form.

DETAILED DESCRIPTION OF THE PREFERRED EMBODIMENTS

A description of the preferred embodiments of the present invention will now be presented with reference to FIGS. 1A–13.

Figure 1A:
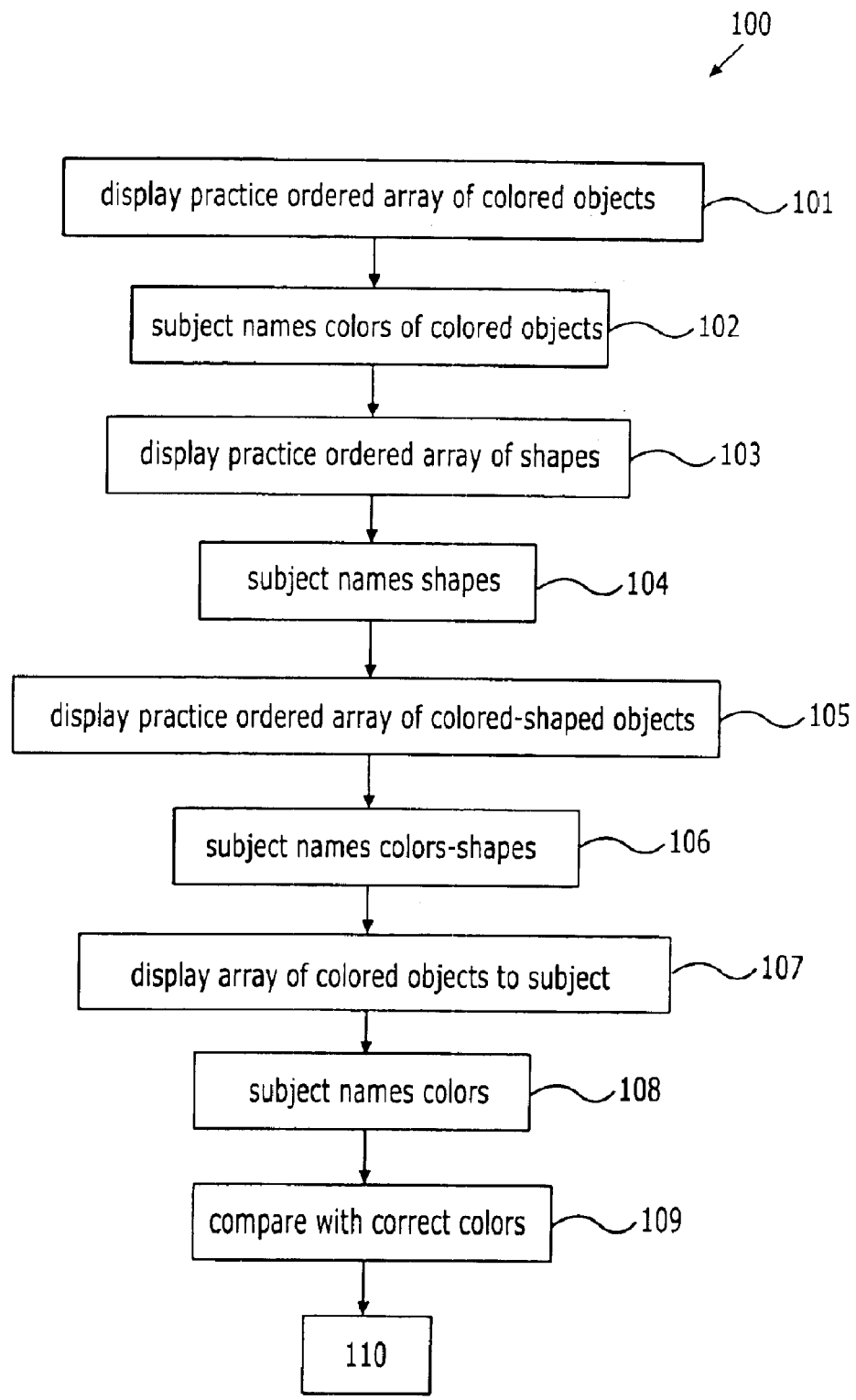
FIGS. 1A–1D is a flow chart of a preferred embodiment of the present invention.
Figure 1B:
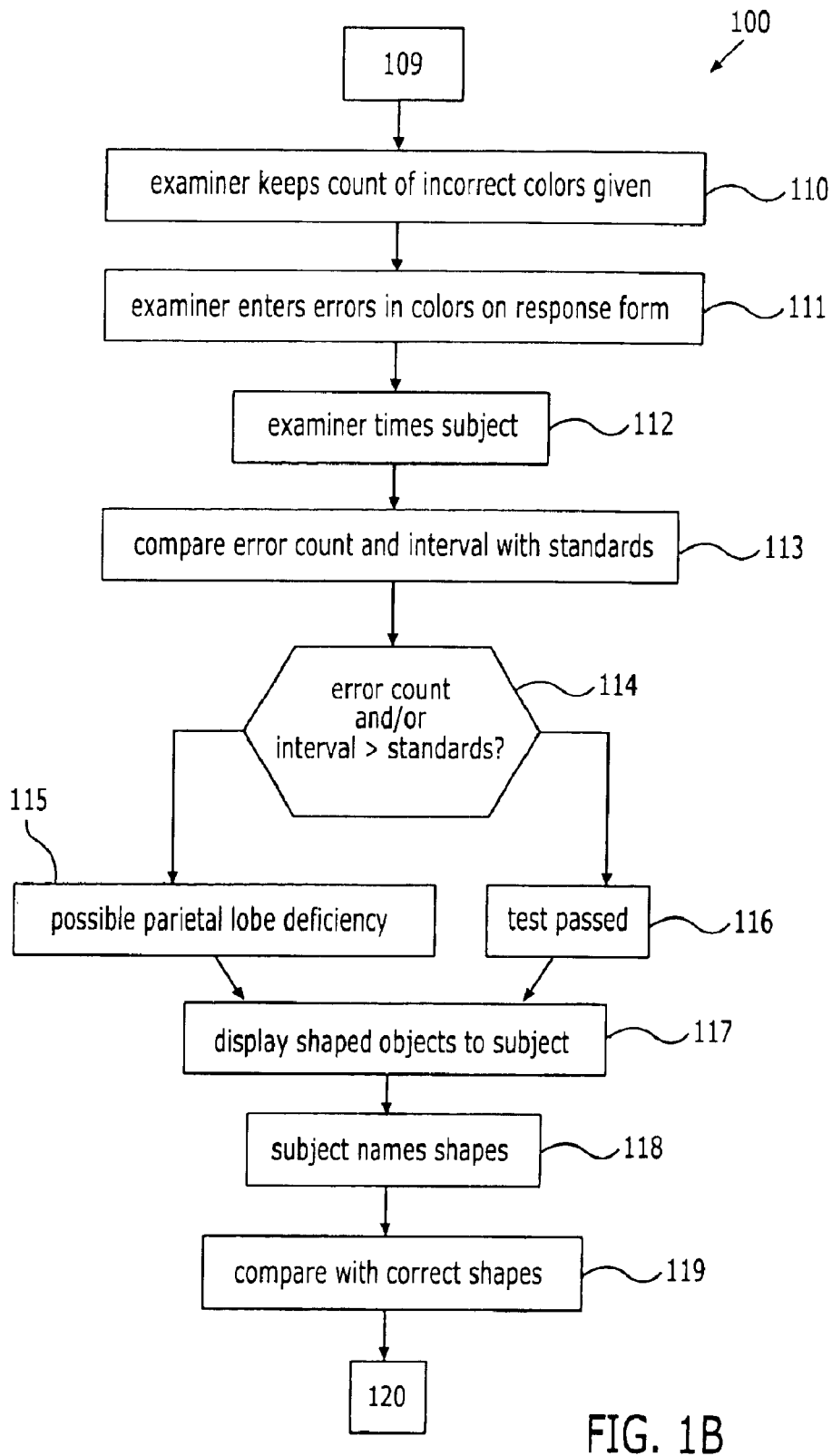
Figure 1C:
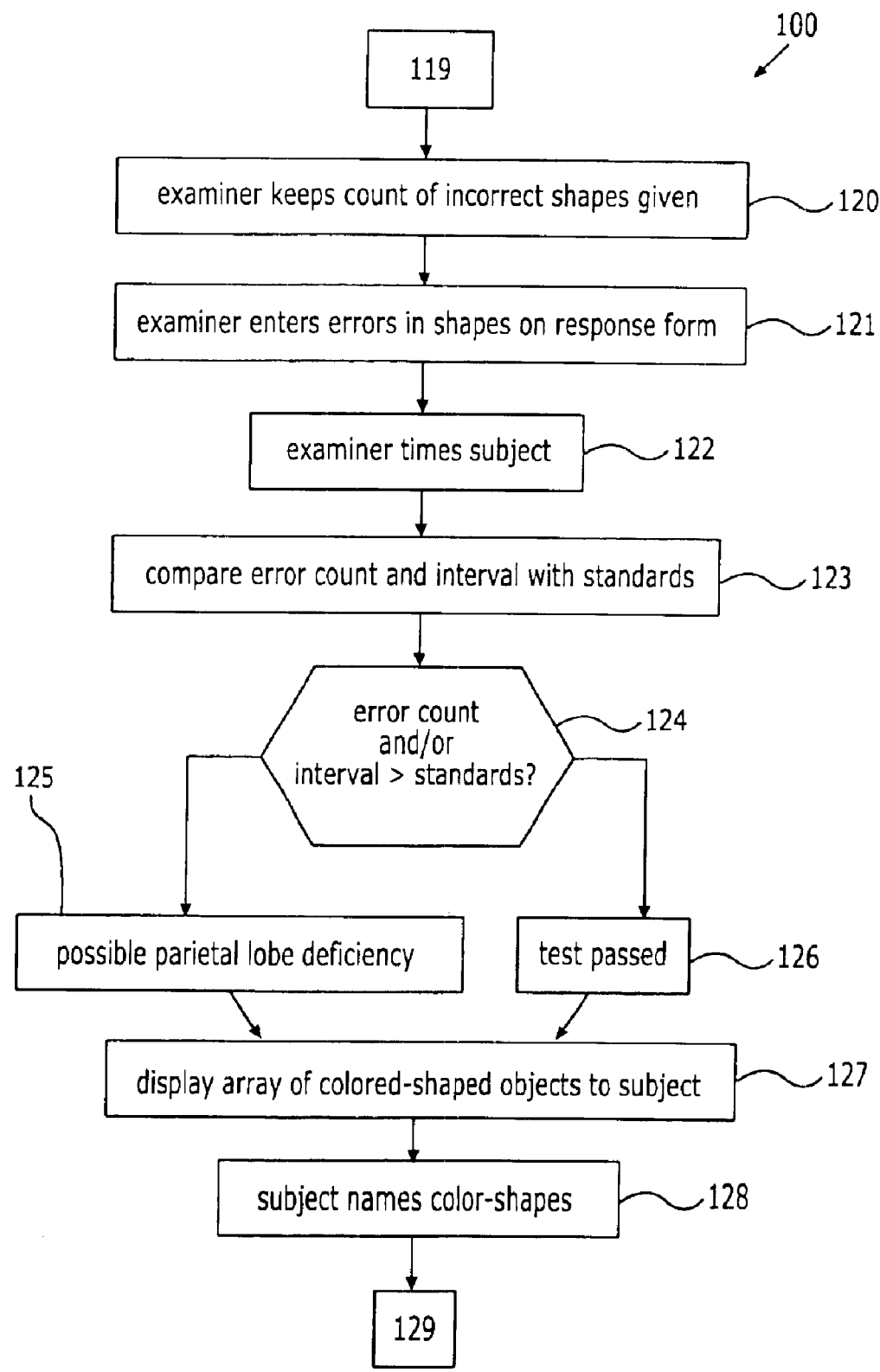
Figure 1D:
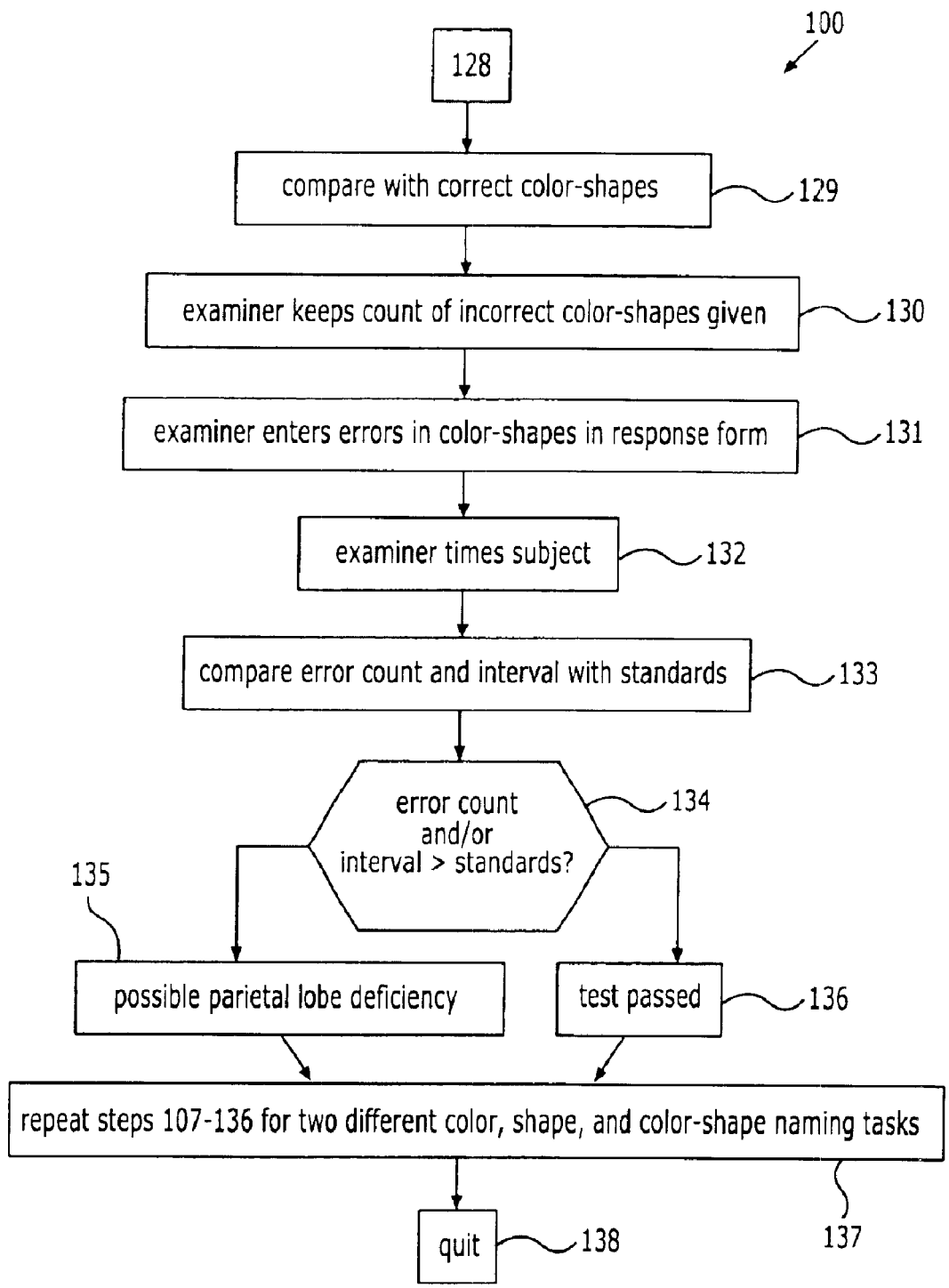
Figure 1E:
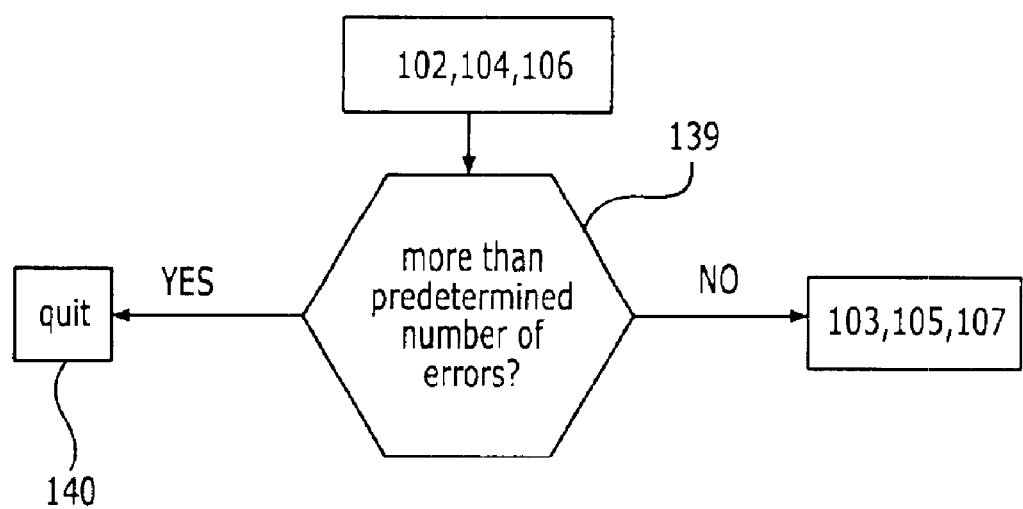
FIG. 1E is a flow chart of an alternate embodiment for part of the method of FIGS. 1A–1D.
Figure 2A:
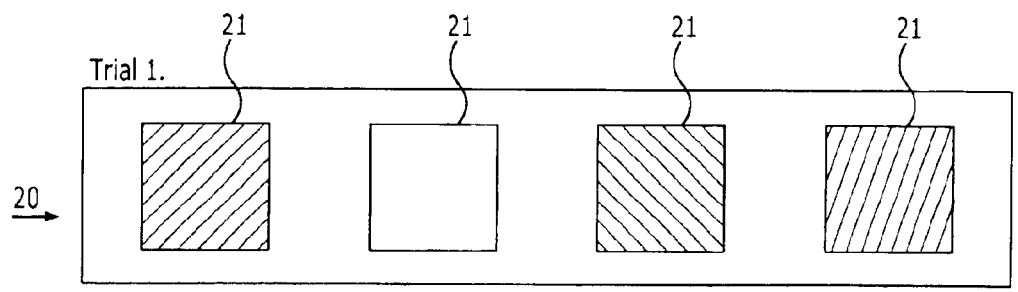
FIGS. 2A, 2B illustrate exemplary displays for the first and second portion of a practice test, respectively.
Figure 2B:
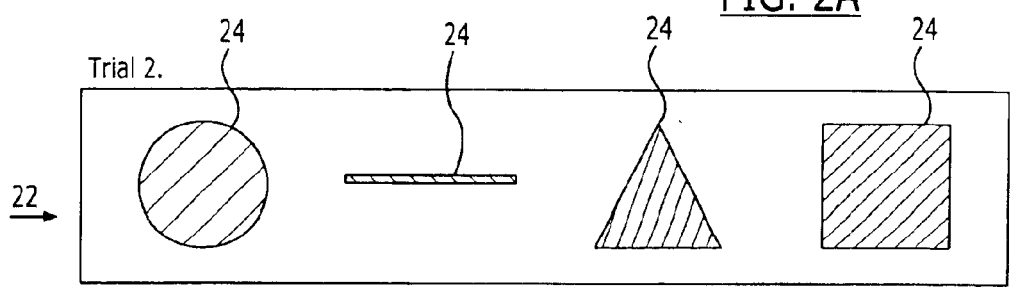

The present invention includes a test, system, and method for testing parietal lobe function in a subject, typically administered by an examiner. The method 100, illustrated in flowchart form in FIGS. 1A–1D, includes a practice phase having three portions. The practice phase first portion comprises the steps of displaying to the subject a practice ordered array of objects having a variety of colors (FIG. 1A; block 101). This practice ordered array 20 in FIG. 2A comprises a row 20 of colored squares 21, the colors here indicated by shading, as the drawing is in black and white. Preferably these objects 21 have a common shape, here, square, although this is not intended as a limitation. The subject is then prompted to practice by naming the object colors sequentially in order (block 102).

The practice phase second portion comprises the steps of displaying to the subject a practice ordered array of objects having a variety of shapes (block 103). This practice ordered array of objects in FIG. 2B comprises a row 22 of outlined shapes 24. Preferably these shapes have no color, although this is not intended as a limitation. The subject is prompted to practice by naming the object shapes sequentially in order (block 104).

Figure 3:
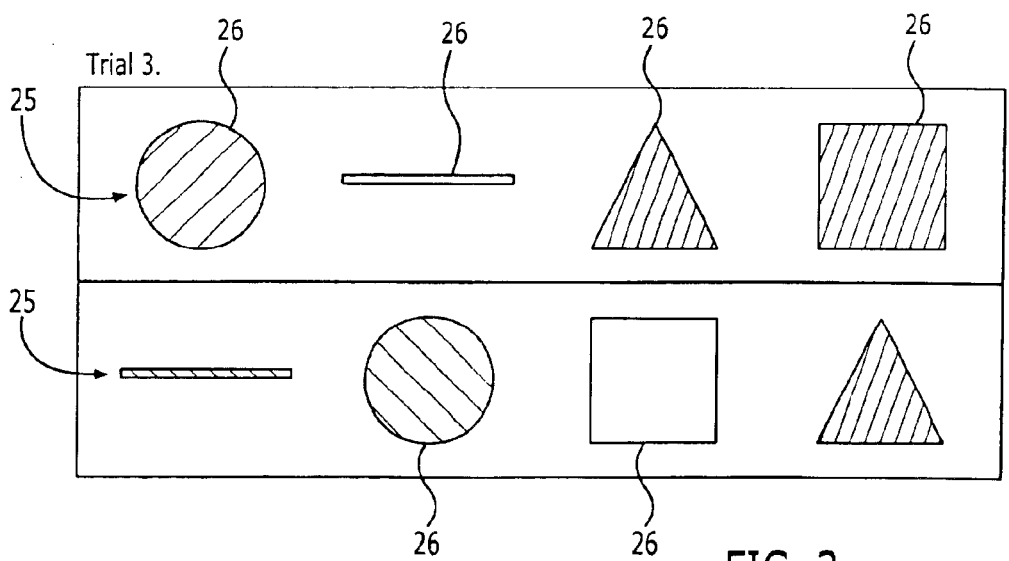
FIG. 3 illustrates an exemplary display for the third portion of a practice test.

The third portion of the practice phase of the test comprises the step of displaying a practice ordered array of objects having a variety of shapes and a variety of colors (block 105). In FIG. 3 the practice ordered array of objects having a variety of shapes and a variety of colors includes two rows 25 of four objects 26 each. The subject is prompted to practice by naming the shapes and colors sequentially in order in both rows (block 106).

In an alternate embodiment (FIG. 1E), during the practice phase, following one of the naming steps (blocks 102, 104, 106), if the subject makes more than a predetermined number of errors (block 139), the test administration is halted (block 140). If fewer than a predetermined errors is made (block 139), the test continues to the respective step (block 103, 105, 107, respectively). This occurs if the subject is apparently unable to complete the test satisfactorily.

In the main phase of the test administration method 100, three trials are administered to determine a level of adequacy in naming visual stimuli featured in the test: two single-dimension measures and one combination-naming task. The single-dimension tests are used to determine if motor-system dysfunction (e.g., dysarthria, apraxia), visual or perceptual deficits (e.g., color blindness, discrimination), or general slowness in responding causes a decrease in naming speed across the tasks. The speed and accuracy for single-dimension naming can be related directly to evidence from neuroimaging of regional cerebral blood flow to cortical activation of the occipital lobes.

Preferably the primary diagnostic measures are featured as the dual-dimension naming test of each task set. Continuous dual-dimension naming requires rapid and accurate perceptual and conceptual shifts between the dimensions and their associated semantic fields, known to occupy separate regions of the cortex. The scores obtained during color-form combination naming have been related directly to evidence of cortical activation of the parietal lobes associated with deactivation of the prefrontal lobes.

Figure 4:
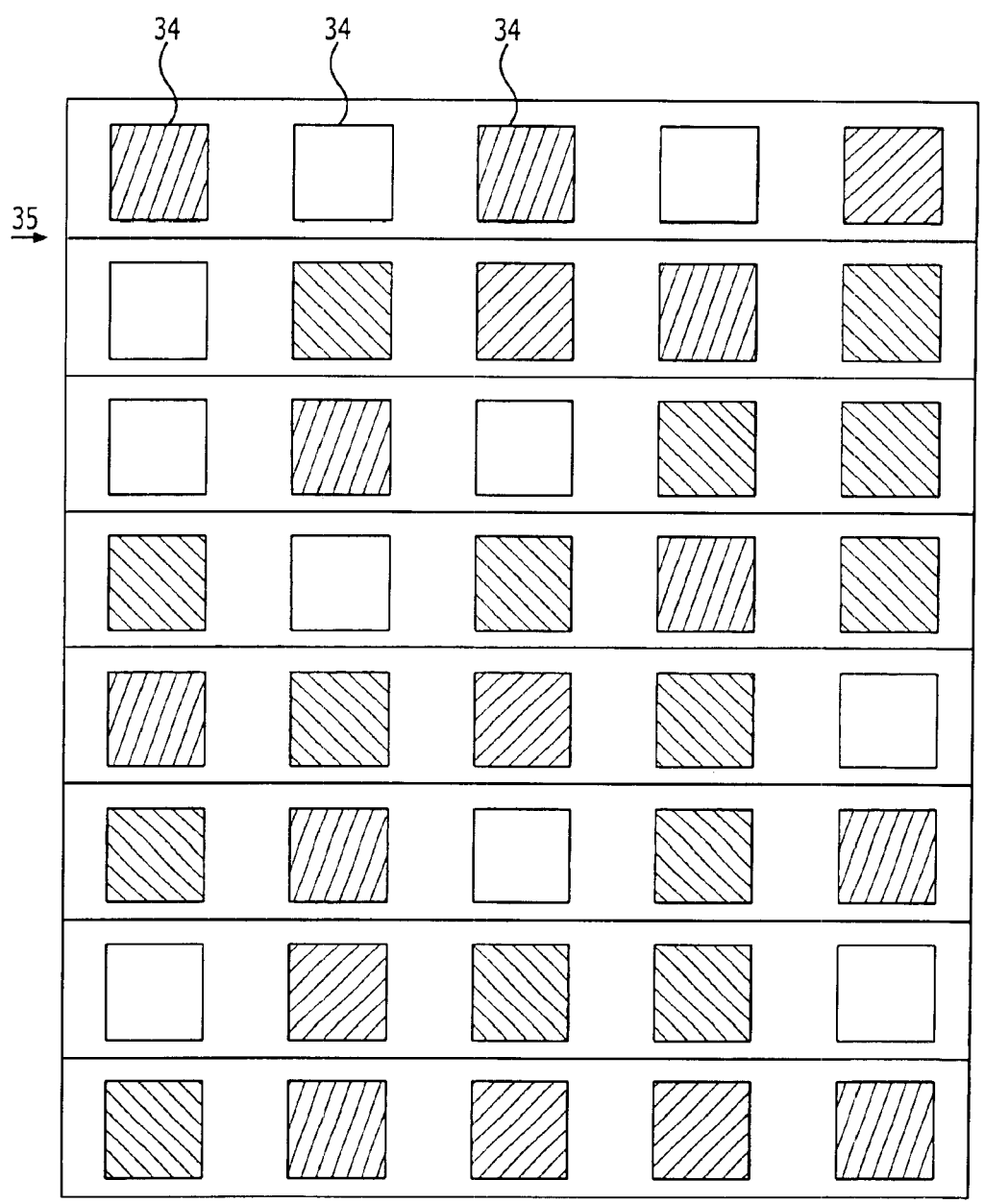
FIG. 4 illustrates an exemplary display for the first portion of the test.

A first ordered array of objects having a variety of colors is displayed to the subject (block 107). Preferably the objects have a substantially analogous shape, here, squares, although this is not intended as a limitation. In FIG. 4 is illustrated an exemplary display of 40 squares 34 arrayed in a 5×8 matrix 35. As above, the squares 34 would preferably be colored, but are shown here with different shadings to represent colors. Preferably each object has a unitary shape, here, a square, although this is not intended as a limitation.

The subject is then prompted to name the object colors sequentially in order (block 108). The named object colors are then compared with the correct object colors (block 109). The examiner keeps a count of each incorrect answer, both self-corrected 71 and uncorrected 72, as well as the total number of errors 73 (block 110), and enters them on the Response Form 70 (FIG. 7; block 111) when all colors have been named on FIG. 4. Also, an interval taken by the subject to complete naming the object colors is timed, the interval 74 entered into the Response Form 70 (block 112).

The color-naming error count and interval are then compared with a predetermined color-naming error count and interval (block 113). An accuracy performance range 76 is indicated on the Response Form 70, as well as a time performance range 76, with blocks provided for ranges of normal, worse than normal, and non-normal performance. The maintained color-naming error count and/or the timed interval being greater than the predetermined color-naming error count and interval (block 114) is indicative of a possible parietal lobe function deficiency (block 115). If these criteria are satisfied (block 114), the subject passes this portion of the test (block 116).

Figure 5:
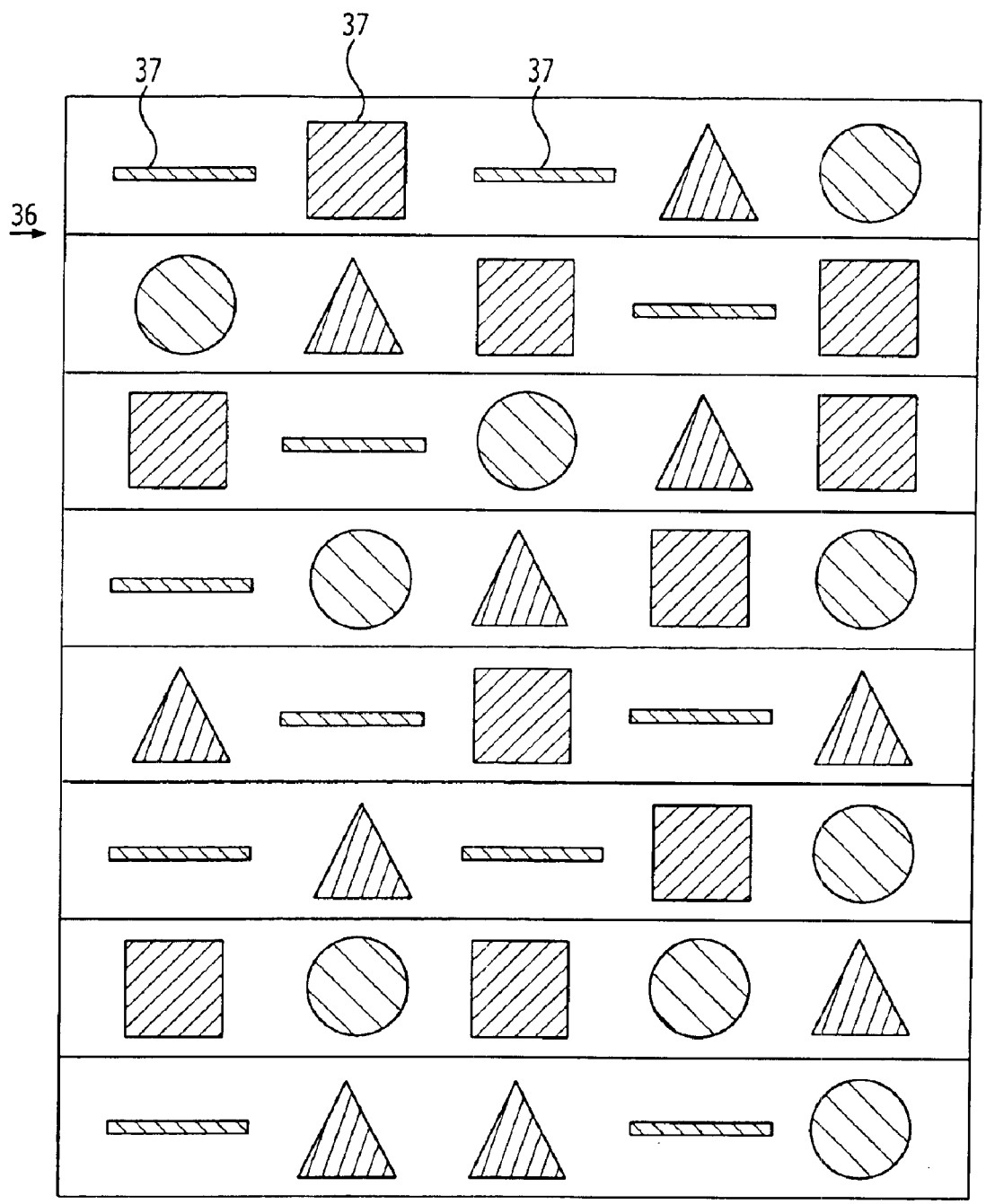
FIG. 5 illustrates an exemplary display for the second portion of the test.

In another portion of the method 100, a second ordered array of objects having a variety of shapes is displayed to the subject (block 117). An exemplary display for this portion of the test 100 is illustrated in FIG. 5, comprising a 5×8 matrix 36 of black shapes 37, although this is not intended as a limitation.

The subject is then prompted to name the object shapes sequentially in order (block 118). The named object shapes are compared with the correct object shapes by the examiner (block 119). The examiner keeps a count of each incorrect answer, both self-corrected 77 and uncorrected 78, as well as the total number of errors 79 (block 120), and enters them on the Response Form 70 (FIG. 7; block 121) when all shapes have been named on FIG. 5. Also, an interval taken by the subject to complete naming the object shapes is timed, the interval 80 entered into the Response Form 70 (block 122).

The shape-naming error count and interval are then compared with a predetermined shape-naming error count and interval (block 123). An accuracy performance range 81 is indicated on the Response Form 70, as well as a time performance range 82. The maintained shape-naming error count and/or the timed interval being greater than the predetermined shape-naming error count and interval (block 124) is indicative of a possible parietal lobe function deficiency (block 125). If these criteria are satisfied (block 124), the subject passes this portion of the test (block 126).

Figure 6:
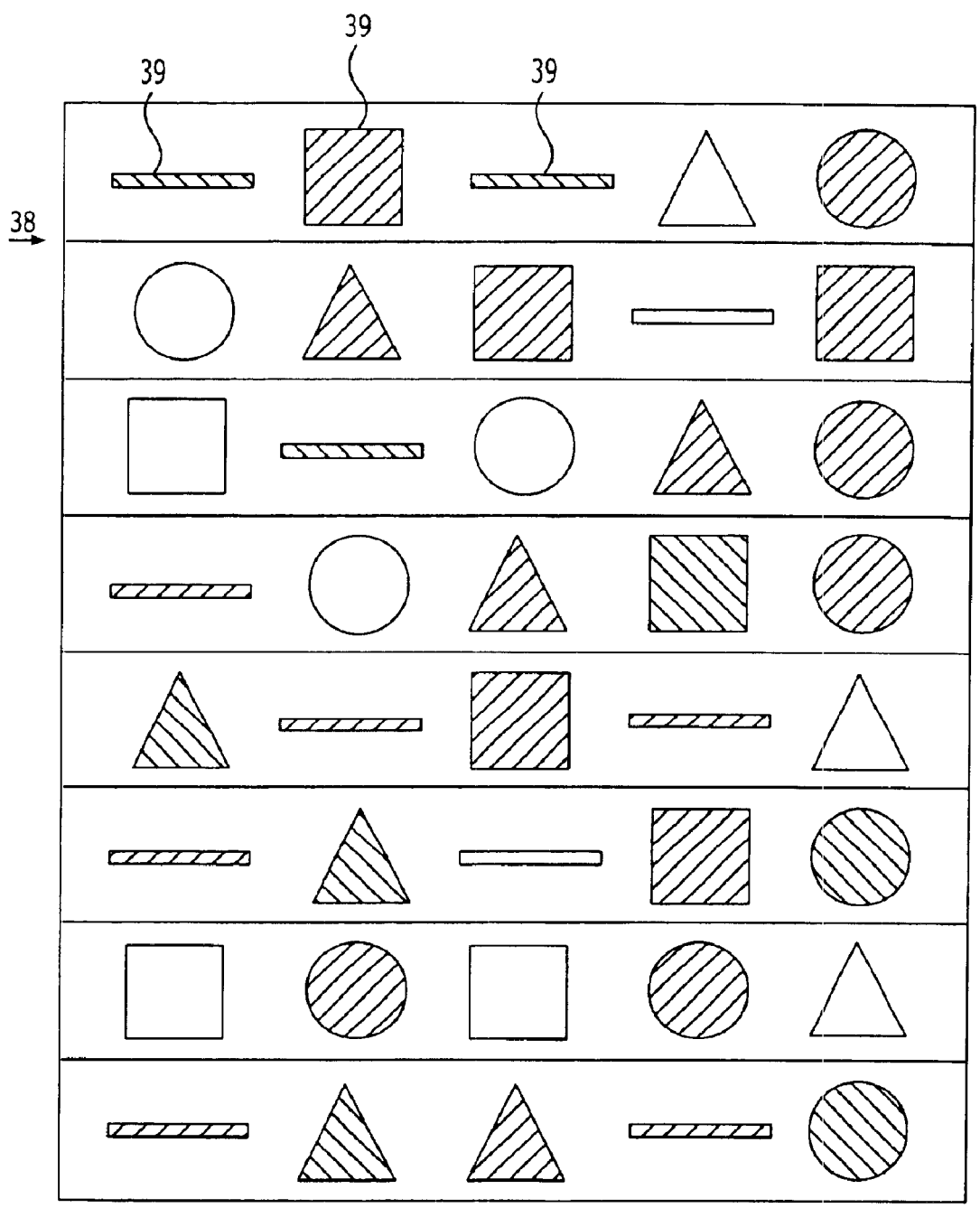
FIG. 6 illustrates an exemplary display for the third portion of the test.

In yet a further portion of the method 100, a third ordered array of objects having a variety of shapes and a variety of colors is displayed to the subject (block 127). Such an exemplary array 38 is illustrated in FIG. 6, comprising a 5×8 matrix of objects 39.

The subject is then prompted to name the object colors and shapes sequentially in order (block 128). The named object colors and shapes are compared with the correct object colors and shapes by the examiner (block 129). The examiner keeps a count of each incorrect answer, both self-corrected 83 and uncorrected 84, as well as the total number of errors 85 (block 130), and enters them on the Response Form 70 (FIG. 7; block 131) when all colors and shapes have been named on FIG. 6. Also, an interval taken by the subject to complete naming the object colors and shapes is timed, the interval 86 entered into the Response Form 70 (block 132).

The color- and shape-naming error count and interval are then compared with a predetermined color- and shape-naming error count and interval (block 133). The maintained color- and shape-naming error count and/or the timed interval being greater than the predetermined shape-naming error count and interval (block 134) is indicative of a possible parietal lobe function deficiency (block 135). If these criteria are satisfied (block 134), the subject passes this portion of the test (block 136).

Figure 13:
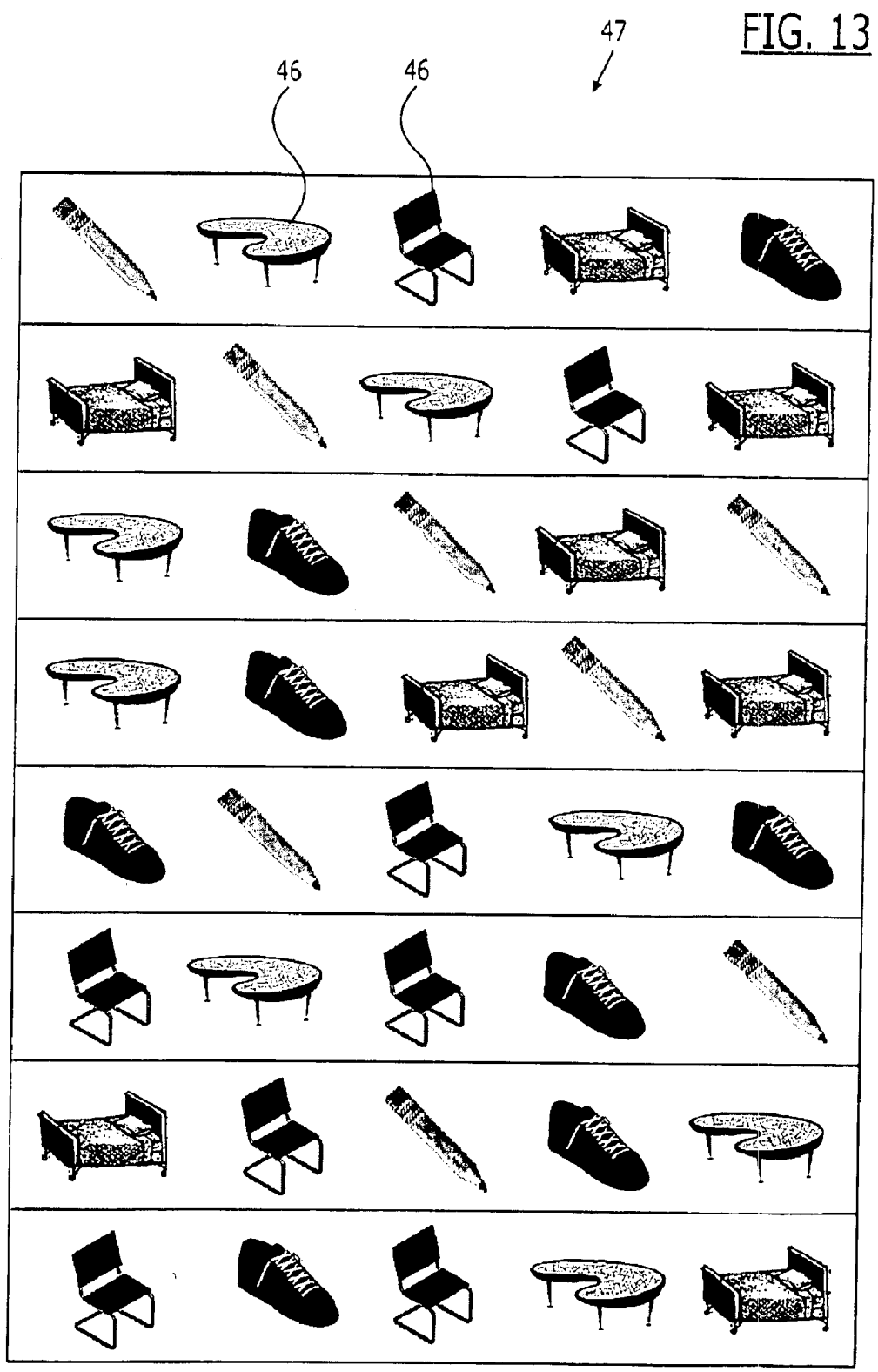
FIG. 13 illustrates an exemplary display of a household object array.

Preferably the method 100 is repeated (block 137), using, for example, a variety of other objects. A total of two color-object tasks are preferably given. Other exemplary objects may include, but are not intended to be limited to, letters 40 in a 5×8 array 41 (FIG. 10), numbers 42 in a 5×8 array 43 (FIG. 11), animals 44 in a 5×8 array 45 (FIG. 12), and household objects 46 in a 5×8 array 47 (FIG. 13).

In a preferred embodiment, the test is terminated after three presentations of color, shape, and color-shape arrays (block 138).

At least two of the task sets including color-form, color-number, and color-letter should preferably be given to obtain evidence of parietal lobe dysfunction. The color-animal and color-object tasks may be used as alternatives for the color-form task; these address working memory capacity and executive attention, which are believed to be important components of fluid reasoning and correlate with performances on higher-order cognitive tasks involving expressive language, word finding, reading comprehension, and complex learning and reasoning.

Figure 7B:
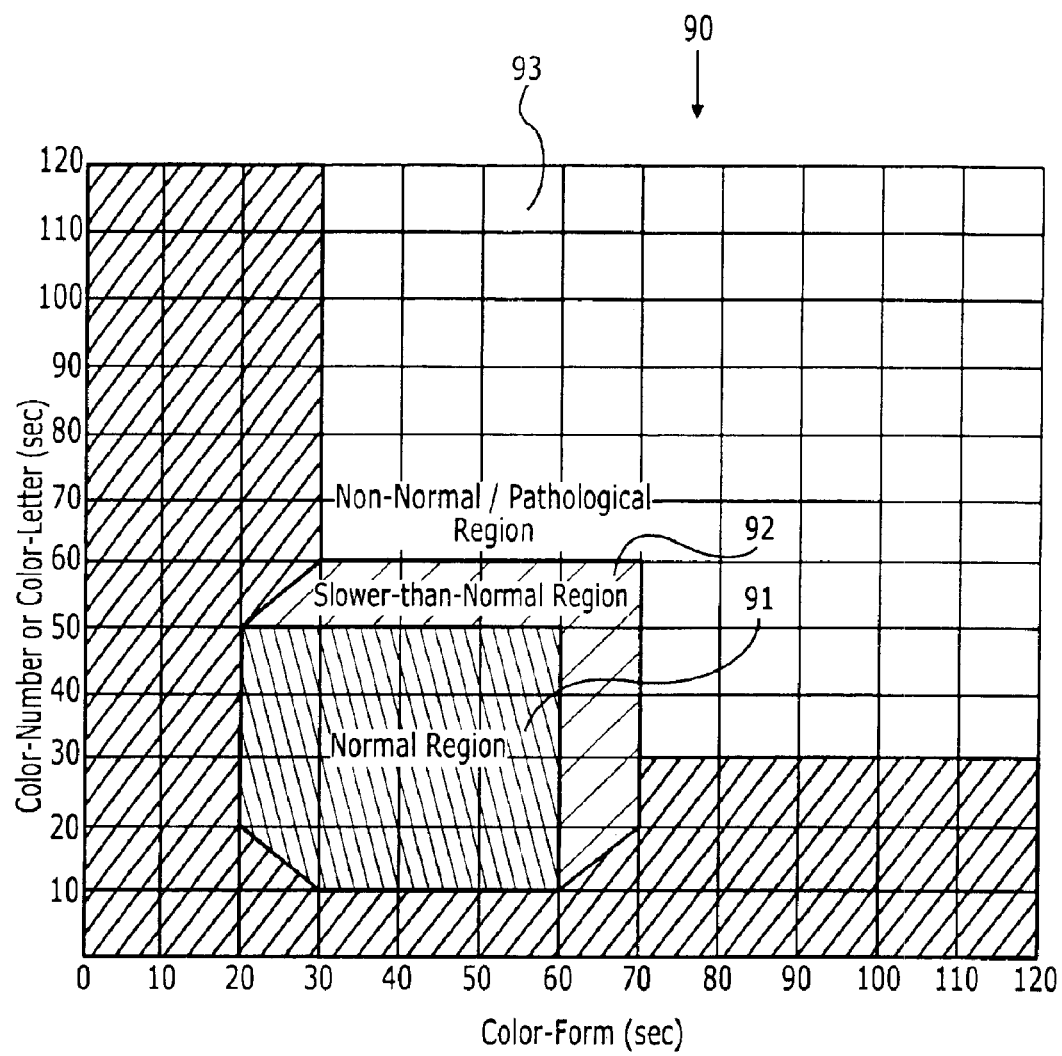
FIG. 7B illustrates an exemplary time performance graph.

An exemplary chart 90 for placing the subject in a normality region is given in FIG. 7B, which comprises a two-dimensional comparison of subject data. In this graph two timed intervals form the ordinate and abscissa of the graph, and the subject is placed in a range of normal 91, slower than normal 92, or non-normal/pathological 93 based upon performance in two sectors of the test. It will be understood by one of skill in the art that any of the collected subject data can form such a two-dimensional representation, and that other data collected on the tests of the present invention may be used to form such a graph. Similarly, more than two dimensions may be used for such an evaluation, wherein n-dimensional modeling may be performed on a computer, for example. The three time performance ranges indicate:

1. Normal/typical.
2. Slower than normal, not clearly indicative of non-normal or pathological conditions such as dementia. The subject may be considered at risk and should be retested and/or referred for further neurological assessment.
3. Non-normal or pathological, suggests Alzheimer's disease or dementia. The subject should be referred for a CT scan, at minimum, to exclude any morphological changes or brain abnormalities before a diagnosis can be made.

The following exemplary tables provide ranges for naming times that are applicable for men and women between the ages of 15 and 75+ years:

TABLE 1

Naming time (sec) criterion score ranges for combination-naming tests.

| Test | Normal | Slower than Normal | Non-Normal |
| --- | --- | --- | --- |
| Color-form | <60 | 60–70 | >70 |
| Color-number | <50 | 50–60 | >60 |
| Color-letter | <50 | 50–60 | >60 |
| Color-animal | <55 | 55–65 | >65 |
| Color-object | <55 | 55–65 | >65 |

TABLE 2

Naming time (sec) criterion score ranges for single-dimension naming tests.

| Test | Normal | Slower than Normal | Non-Normal |
| --- | --- | --- | --- |
| Color | <25 | 25–35 | >35 |
| Form | <30 | 30–40 | >40 |
| Number | <20 | 20–30 | >30 |
| Letter | <20 | 20–30 | >30 |
| Animal | <35 | 35–40 | >40 |
| Object | <35 | 35–40 | >40 |

There are three accuracy performance ranges for men and women between the ages of 15 and 75+. When adolescents and adults do not meet the criteria for normal naming accuracy, there is generally evidence of neurological dysfunction associated with parietal lobe dysfunction such as in Alzheimer's disease, traumatic brain injury, Tourette syndrome, or ADHD. In those cases, the naming errors frequently reflect perseveration across adjacent stimuli.

TABLE 3

Criterion Score Ranges for Naming Accuracy (Number of Errors)

| Test | Normal | More Errors Than Normal | Non-Normal |
| --- | --- | --- | --- |
| Color-form | <2 | 3–4 | >5 |
| Color-number | <2 | 3–4 | >5 |
| Color-letter | <2 | 3–4 | >5 |
| Color-animal | <2 | 3–4 | >5 |
| Color-object | <2 | 3–4 | >5 |

Response time and accuracy for each combination-naming test provide the basis for interpreting and describing a subject's test performance. The subject's naming time for each test should be compared with the criterion ranges to identify the range within which the performance lies. Subjects whose naming times lie in the slower-than-normal or non-normal range should be referred for further assessment and/or CT scan to rule out morphological changes or brain abnormalities.

Any combination-naming accuracy score out of the normal range in each task set should be compared with the naming time performance range for that test. In some cases, naming time may be within the normal range, while naming accuracy is out of the normal range. This may occur with ADHD, lack of inhibition (impulsivity), organic brain injury, or aphasia. In these cases, testing should be repeated after a short rest period. If the subject's naming accuracy is still out of the normal range, an assessment for specific word-finding difficulties (dysnomia) should be administered). When naming accuracy measures are in the non-normal range, the errors are often perseveration, substitutions, or omissions and may require further exploration.

If the single-dimension naming times are within the normal range, but the dual-dimension naming times lie outside the normal range, the results match the performance pattern of adults with verified parietal lobe dysfunction.

If the times for the primary combination-naming tests (color-form, color-number, color-letter) lie within the normal range, the subject passes screening, with no evidence of parietal lobe dysfunction.

Naming times that are in the slower-than-normal range for two of the primary combination-naming tests (color-form and color-number or color-form and color-letter) indicate a slowing of processing speed, which can be seen in developmental disorders (e.g., ADHD, dyslexia, specific language impairments, or Tourette syndrome) or in neurogenic disorders (e.g., TBI or ischemic CVA).

Naming times in the non-normal range for the primary screening tasks indicate:

1. Clinically significant deficits in processing speed, working memory, automaticity and fluency of retrieval and production, and executive memory 2. Deterioration of parietal-lobe functions (e.g., Alzheimer's disease)

3. Pervasive cognitive impairments involving other brain structures (e.g., global dementia)

4. The presence of structural brain abnormalities

In these cases a CT scan is necessary to rule out brain abnormalities (e.g., tumor, CVA, or TBI) that may cause similar naming-speed deficits. In all cases in which Alzheimer's disease is suspected because combination-naming times are in the non-normal range, the subject should be referred for a follow-up evaluation to rule out morphological changes or brain abnormalities.

A deficit in naming speed, especially in adolescents and young adults, may also indicate a developmental language disorder associated with reduced word retrieval and expressive language problems or an acquired language disorder after TBI. In everyday contexts, these deficits are often characterized by word-finding difficulties (dysnomia/anomia), non-fluency (e.g., slow rate of speech, high number of pauses, hesitations, revisions, self-corrections, and circumlocutions, and by disorganization in complex language production. In that case, an in-depth language assessment is indicated.

Naming speed deficits may be indicators of dyslexia. Deficits in naming speed for color-letter combinations, in the presence of normal speed for naming color-form, color-number, color-animal, and/or color-object combinations may reflect a neurolinguistic deficit related to reading difficulties (dyslexia). A color-letter naming speed deficit can occur in isolation, while other combination-naming times are within normal limits in adolescents and adults with dyslexia. A subject with this pattern should be referred for follow-up evaluation for dysnomia and reading disability.

Naming times for the single-dimension stimuli provide a baseline for interpreting the results of each combination-naming task. Preferably three tests are administered, and performance may then be interpreted as follows:

1. If the naming times for three combination-naming tests lie within the non-normal range, there is compelling evidence of parietal lobe dysfunction, and the subject should be referred for follow-up evaluation (e.g., CT scan).

2. If only two tests were administered owing to subject fatigue or another reason, and the naming times for two consecutive combination-naming tests lie in the non-normal range, there is compelling evidence of parietal lobe dysfunction, and a follow-up evaluation should be considered (e.g., CT scan).

3. If the naming times for the primary combination-naming tasks are in the normal range, there is no evidence of parietal lobe dysfunction, and reasons why the subject was referred may be explored.

4. If the naming times for two of the three combination-naming tasks lie within the normal range and one lies outside the normal range, repeat the screening if the performance may reflect anxiety or other emotional reactions. If the performance is consistent, the presence of, for example, ADHD, epilepsy, language impairment, or learning disability may be suggested.

5. If the total naming times for two of the three primary combination-naming tests lie within the non-normal range, examine the content of the tests that were performed within the non-normal range. It appears that the color-form combination-naming time is most sensitive to the early effects of Alzheimer's disease. As the disease progresses, the naming times for the color-number and color-letter combination tests appear to increase, until all performances are within the non-normal range. The observation of such a pattern warrants a referral for follow-up.

Figure 8:
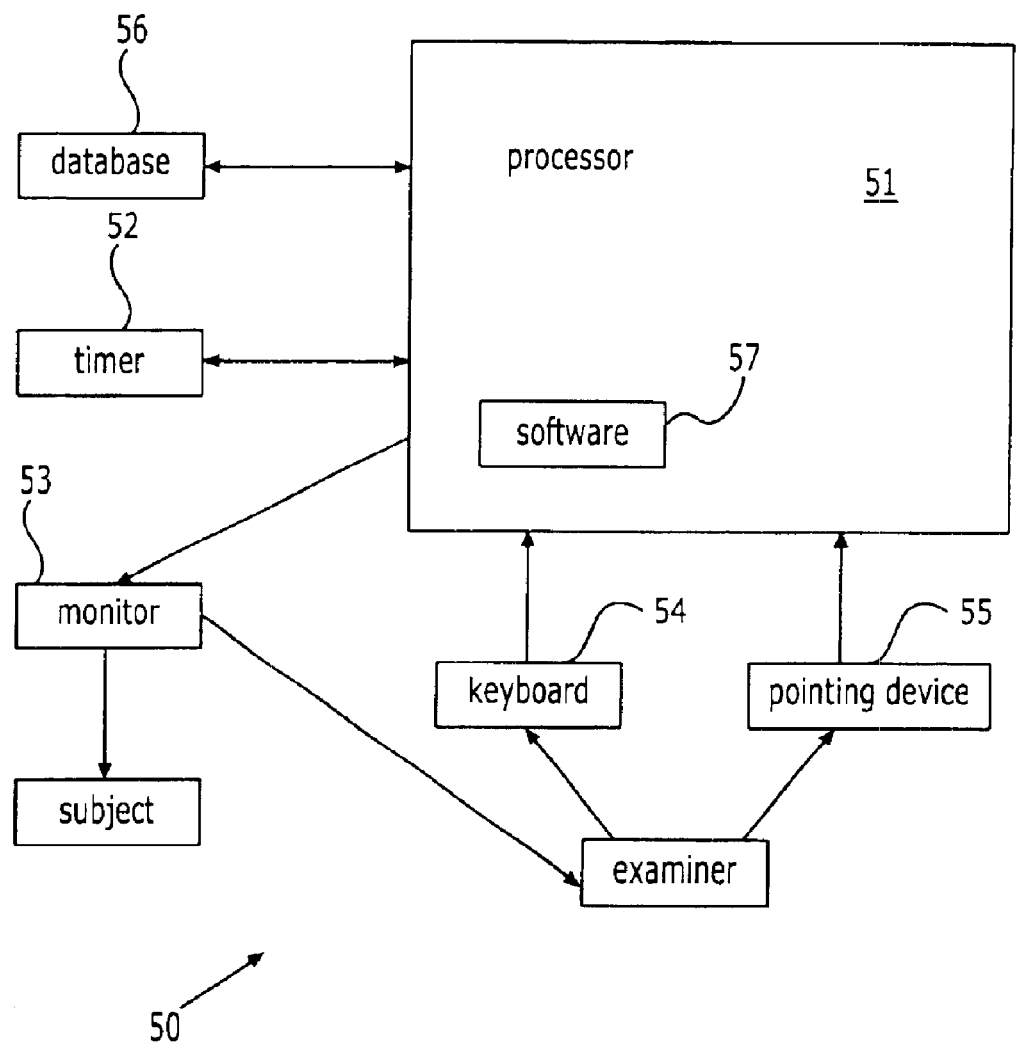
FIG. 8 is a schematic diagram of a computerized test administration system.

In an alternate embodiment of the invention, the parietal lobe function test is delivered and analyzed by a software-driven computerized system 50, a schematic diagram for which is given in FIG. 8. The system 50 comprises a processor 51 in signal communication with a timing device 52, a display device such as a color video monitor 53, and an input device such as a keyboard 54 and/or a pointing device such as a mouse 55. Alternatively, the display and input devices may comprise a unitary device such as a touch screen. One of skill in the art will appreciate that the scope of the invention is not intended to be limited to a particular hardware configuration.

A database 56 is accessible by the processor 51 that contains a set of predetermined standard data against which the current subject's test data may be compared. Such data may include, for example, age-sorted data, or such data arranged or sortable in other desired categories.

A software package 57 is installable on the processor 51 that is adapted to mediate the displaying functions as outlined above for displaying screens analogous to FIGS. 2A–6. The software package 57 is also adapted to receive from an examiner via one of the input devices 54,55 a count of errors in the named object colors, shapes, and color-shapes and to time an interval taken by the subject to complete the naming process by accessing the timing device 52. The software package 57 also accesses the database 56 for a set of predetermined error count and interval data and automatically makes comparisons of the error counts and intervals with the predetermined error count and interval data for determining a possible parietal lobe function deficiency as above.

Following the comparisons, the results are output to the examiner.

Figure 9A:
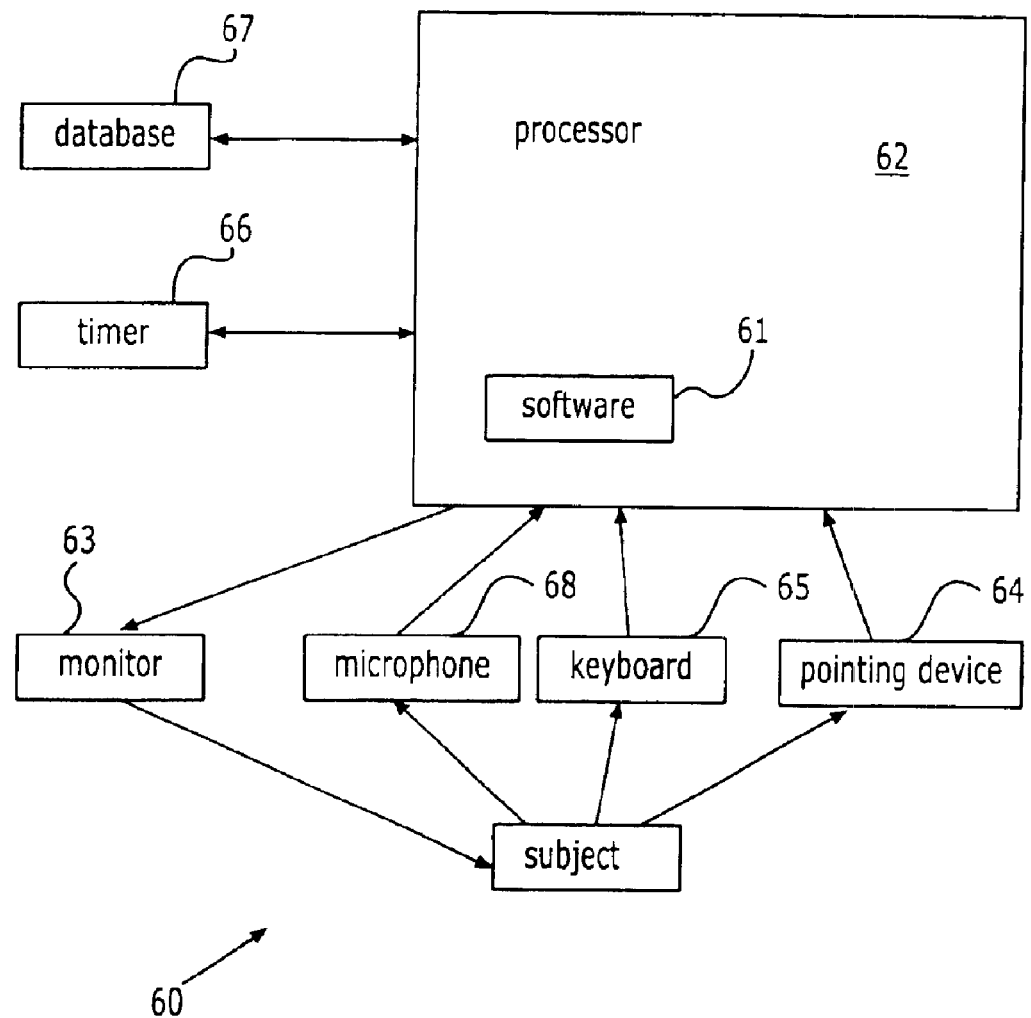
FIG. 9A is a schematic diagram of an automated test administration system.

In yet a further embodiment of the system 60, a schematic for which is shown in FIG. 9A, the test portions may be administered in totally automated fashion, without an examiner, mediated by a software package 61 resident on a processor 62. In this embodiment 60 the software package 61 performs all the displaying, receiving, and analysis functions by interacting directly with the subject, and hence the "examiner" in FIGS. 1A–1D comprises the software package 61 itself. The displays are made on monitor 63, and the subject inputs named objects, shapes, and color-shapes via an input device such as a pointing device 64, keyboard 65, or, most preferably, a microphone 68 in signal communication with the processor 62, in communication with voice-recognition software 69 for interpreting the subject's oral answers. Alternatively, the monitor 63 may comprise a touch screen, serving as input and output device.

In this embodiment 60 the displays include not only the objects to be named for color and/or shape, but also selections, such as a list of colors and shapes to be selected by the subject using the input device. The software package 61 then mediates the timing 66, database 67 access, and analysis functions automatically.

In a subembodiment, the software package 61 comprises a set of rules for determining how and whether to continue the test administration steps based upon performance criteria. For example, if the subject performs below a predetermined minimum level on at least one portion of the practice phase, or on at least one of the trials in the main phase of the test administration, the administration can be halted or re-routed.

Figure 9B:
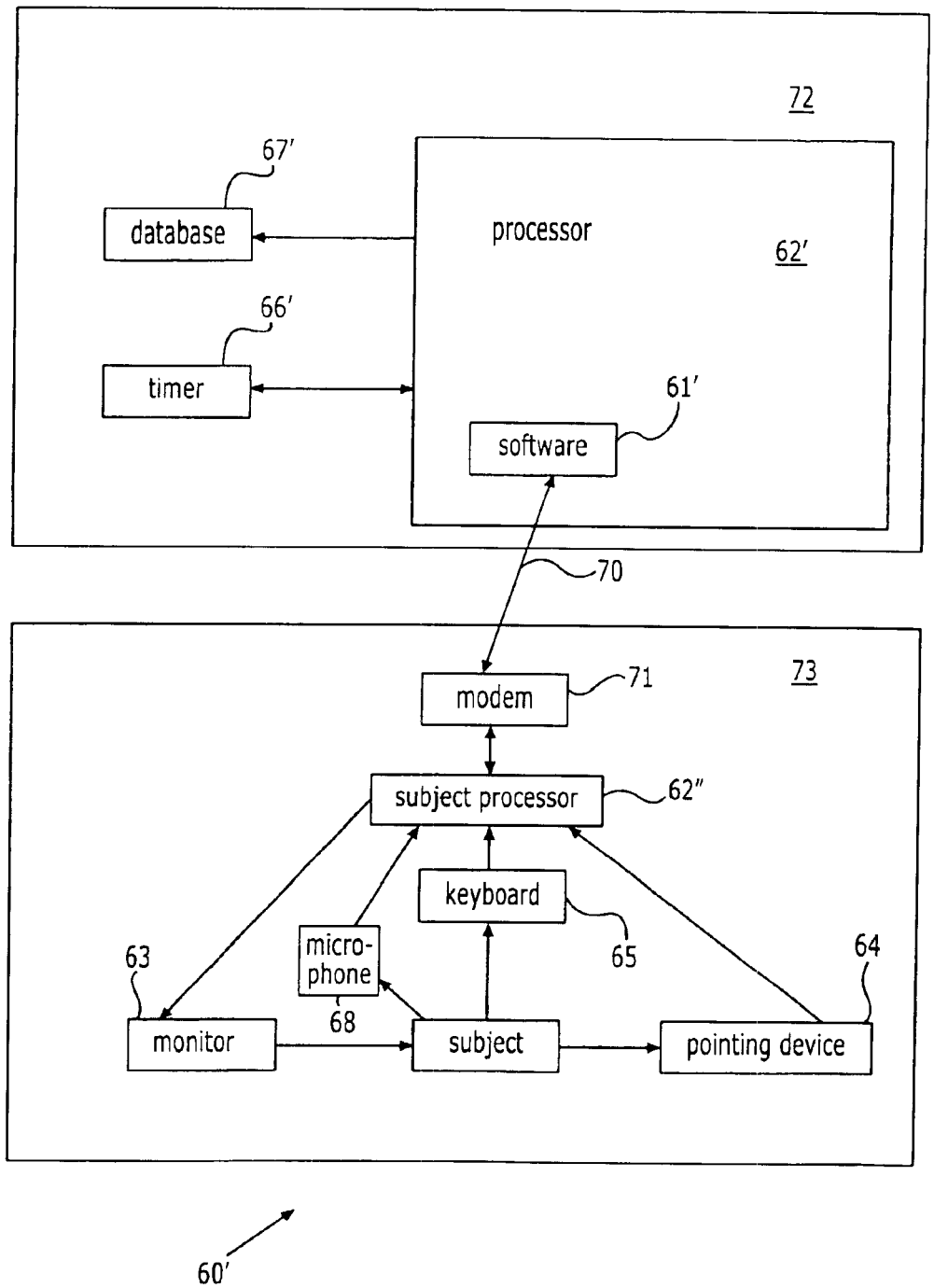
FIG. 9B is a schematic diagram of an automated test administration system administerable over a network.
Figure 10:
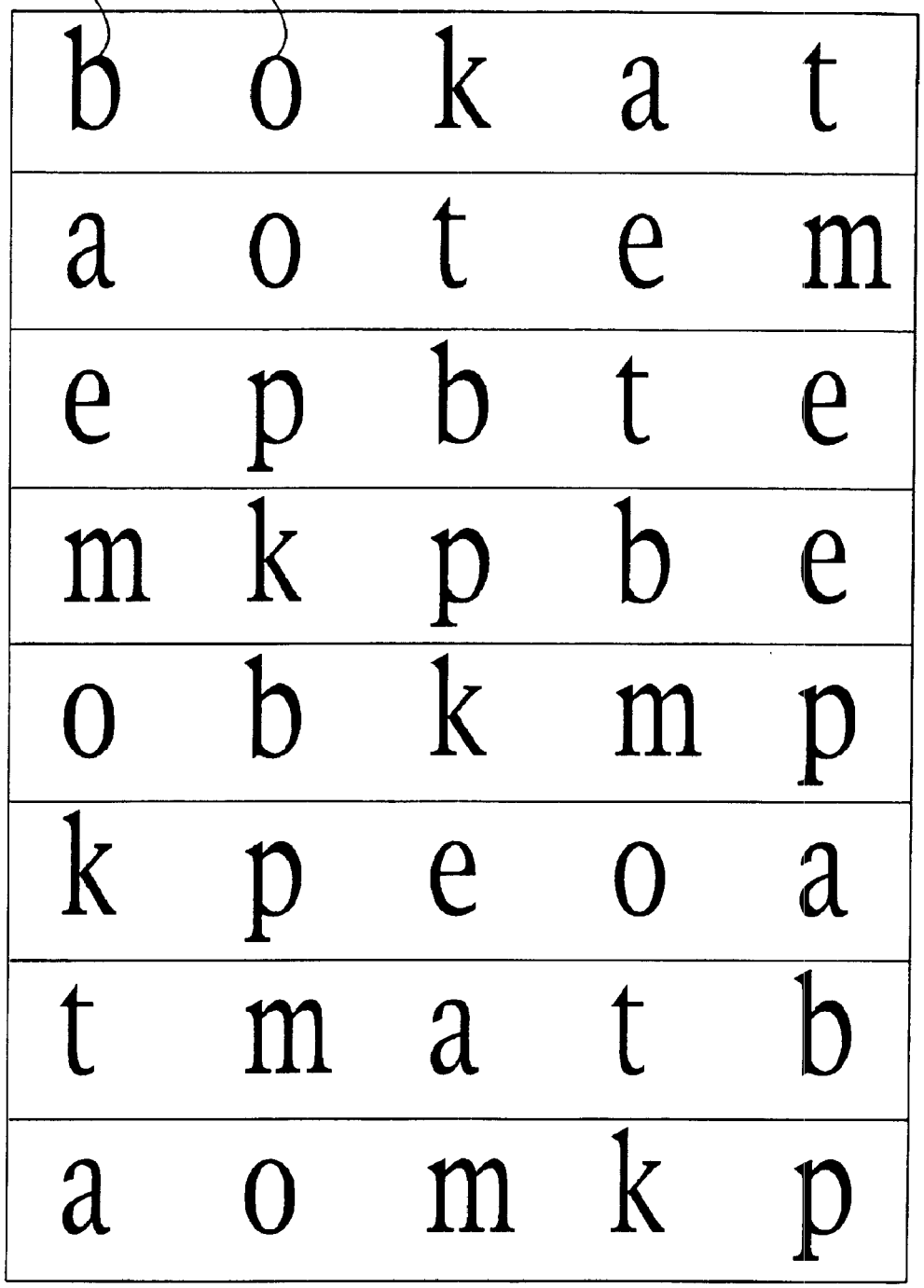
FIG. 10 illustrates an exemplary display of a letter array.
Figure 11:
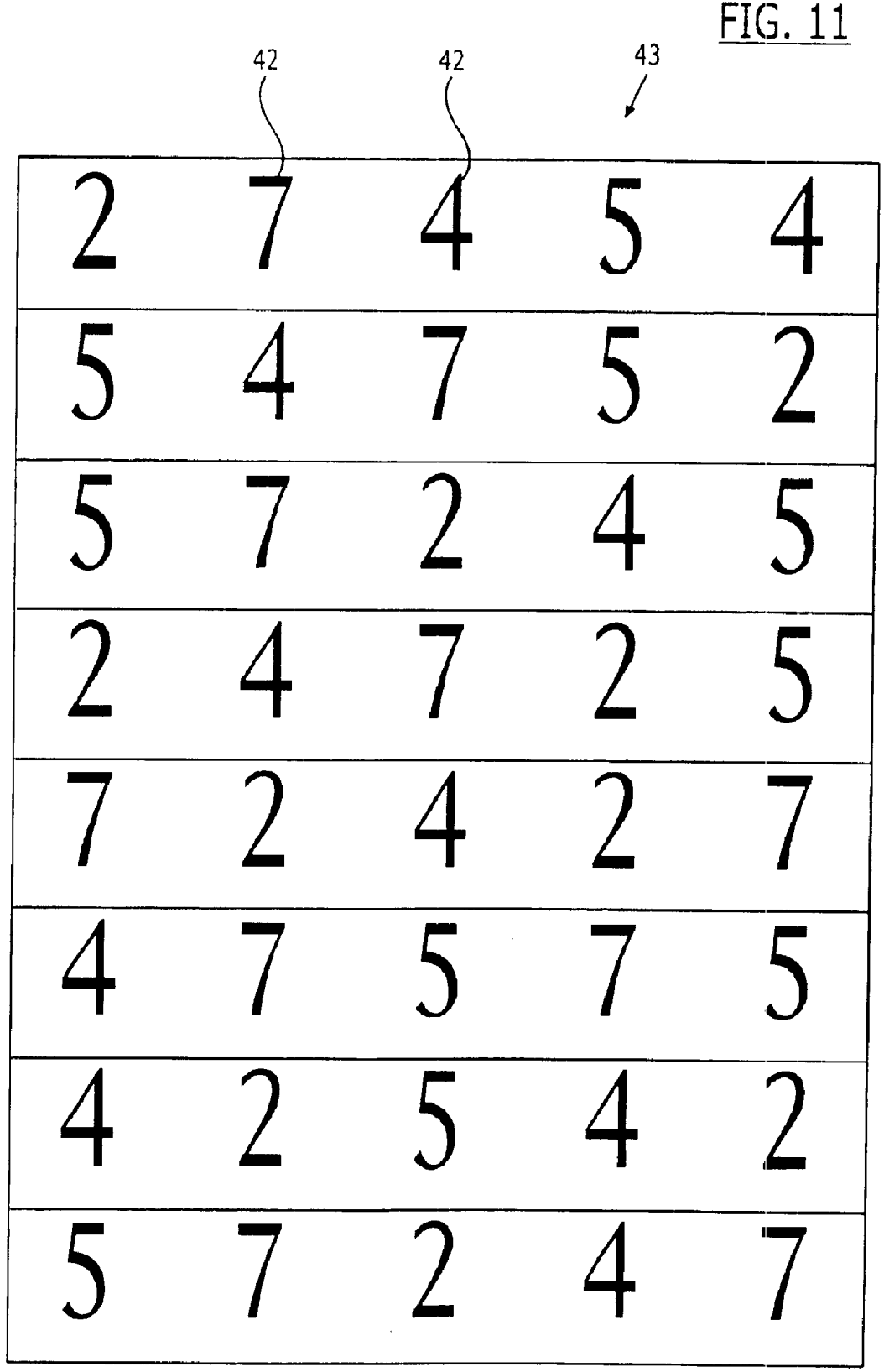
FIG. 11 illustrates an exemplary display of an object array.
Figure 12:
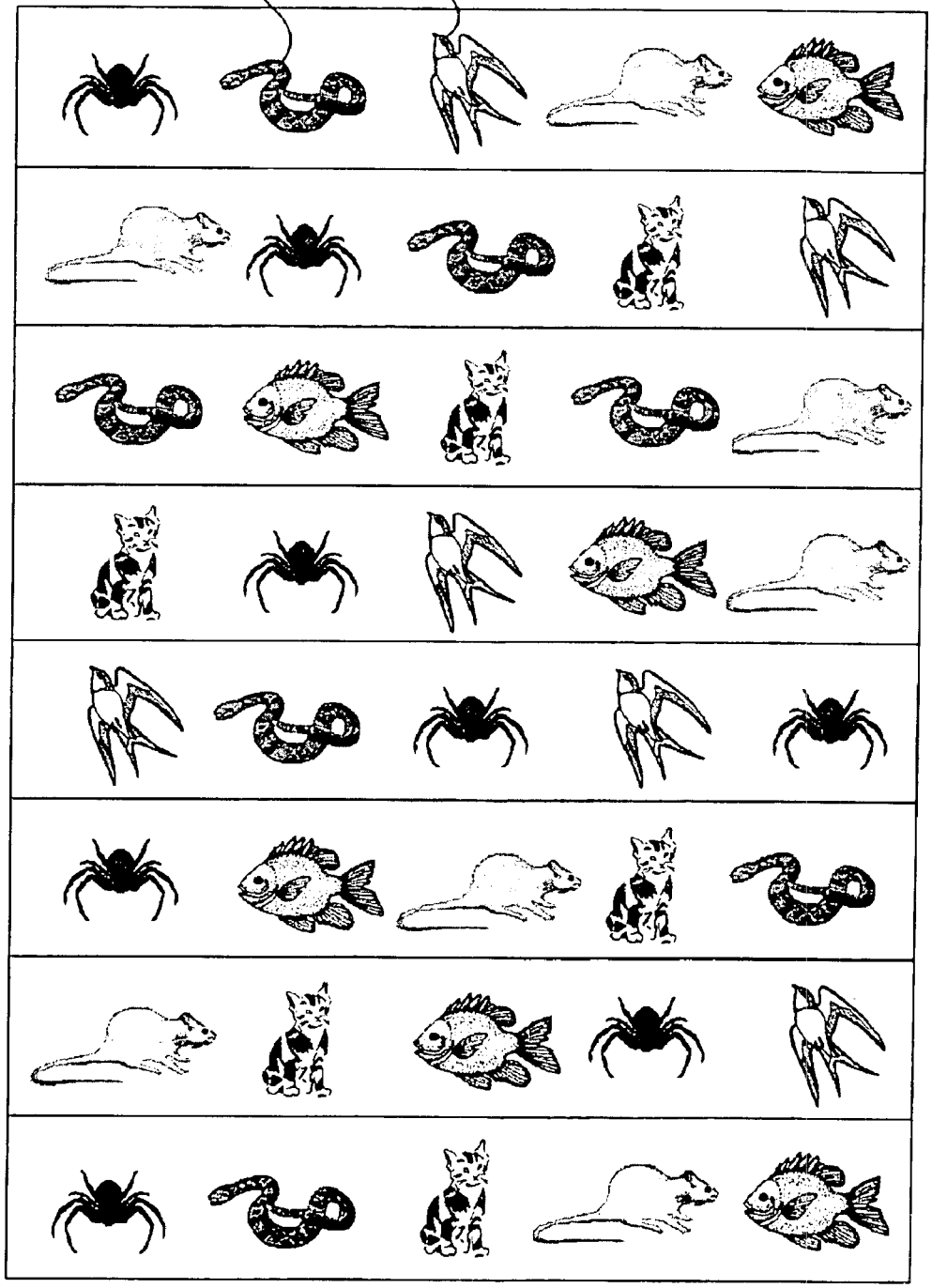
FIG. 12 illustrates an exemplary display of an animal array.

A system 60' analogous to the automated embodiment 60 may also be implemented remotely, such as over an intranet or the Internet 70 (FIG. 9B). In this case 60', the software package 61' is resident on a remote processor 62', in communication with database 67', at a remote site 72. The software package 61' is accessible over a communication means, for example, a modem 71 to, for example, a web site. The subject's processor 62", located at the subject site 73, then interfaces with the software package 61' and mediates the subject interactions via local hardware and software. The invention is not intended to be limited to a particular hardware configuration, and one of skill in the art will recognize alternate equivalent configurations for performing the interaction.

An additional benefit of a remote embodiment 60' is that the results of each administration could be captured as data for subsequent manipulation to update normative data and for research purposes. For example, blind studies could be studied with such amassed data using demographic subject information.

It may be appreciated by one skilled in the art that additional embodiments may be contemplated, including alternate forms of display and of object configurations, and alternate data manipulation and collection methods.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A system for testing parietal lobe function in a subject comprising:

means for displaying to a subject a first ordered array of objects having a variety of colors, each object having a unitary color;

means for prompting the subject to name the object colors sequentially in order;

means for comparing the named object colors with the correct object colors, and maintaining a count of errors in the named object colors;

means for timing an interval taken by the subject to complete naming the object colors;

means for comparing the color-naming error count and interval with a predetermined color-naming error count and interval, a color-naming error count and interval greater than the predetermined color-naming error count and interval indicative of a possible parietal lobe function deficiency;

means for displaying to a subject a second ordered array of objects having a variety of shapes, each object having a unitary color;

means for prompting the subject to name the object shapes sequentially in order;

means for comparing the named object shapes with the correct object colors, and maintaining a count of errors in the named object shapes;

means for timing an interval taken by the subject to complete naming the object shapes;

means for comparing the shape-naming error count and interval with a predetermined shape-naming error count and interval, a shape-naming error count and interval greater than the predetermined shape-naming error count and interval indicative of a possible parietal lobe function deficiency.

2. The system recited in claim 1, wherein the objects in the first ordered array all have a substantially analogous shape.

3. The system recited in claim 1, wherein the objects in the first ordered array all comprise squares.

4. The system recited in claim 1, wherein the objects in the second ordered array all have a substantially analogous color.

5. The system recited in claim 1, further comprising the steps of:

displaying to the subject a third ordered array of objects having a variety of shapes and a variety of colors;

prompting the subject to name the object colors and shapes sequentially in order;

comparing the named object colors and shapes with the correct object colors and shapes;

maintaining a count of errors in the named object colors and shapes;

timing an interval taken by the subject to complete naming the object colors and shapes; and comparing the color- and shape-naming error count and interval with a predetermined color- and shape-naming error count and interval, a color- and shape-naming error count and interval greater than the predetermined color- and shape-naming error count and interval indicative of a possible parietal lobe function deficiency.

6. The system recited in claim 5, further comprising the steps of:

displaying to the subject a fourth ordered array of objects having a variety of shapes and a variety of colors;

prompting the subject to name the object colors and shapes of the fourth ordered array sequentially in order;

comparing the named object colors and shapes of the fourth ordered array with the correct object colors and shapes;

maintaining a count of errors in the named object colors and shapes of the fourth ordered array;

timing an interval taken by the subject to complete naming the object colors and shapes of the fourth ordered array; and comparing the color- and shape-naming error count and interval of the fourth ordered array with a predetermined color- and shape-naming error count and interval, a color- and shape-naming error count and interval greater than the predetermined color- and shape-naming error count and interval indicative of a possible parietal lobe function deficiency.

7. The system recited in claim 6, further comprising the step of performing a two-dimensional comparison of subject data for determining a possible parietal lobe deficiency, the subject data comprising at least one of color- and shape-naming error count for the third ordered array versus color- and shape-naming error count for the fourth ordered array and color- and shape-naming interval for the third ordered array versus color- and shape-naming interval for the fourth ordered array.

8. The system recited in claim 1, wherein, if a possible parietal lobe function deficiency is indicated by at least one of the color-naming error count and interval and the shape-naming error count and interval comparing steps, recommending additional assessment of the subject.

9. The system recited in claim 1, further comprising the step of performing a two-dimensional comparison of subject data for determining a possible parietal lobe deficiency, the subject data comprising at least one of color-naming error count versus shape-naming error count and color-naming interval versus shape-naming interval.

10. A parietal lobe function testing system comprising:

means for displaying to a subject a first ordered array of objects having a variety of colors, each object having a unitary color;

means for maintaining a count of errors in the named object colors;

a timer for timing an interval taken by the subject to complete naming the object colors;

a set of predetermined color-naming error count and interval data against which to compare the color-naming error count, a color-naming error count and interval greater than the predetermined color-naming error count and interval indicative of a possible parietal lobe function deficiency;

means for displaying to the subject a second ordered array of objects having a variety of shapes;

means for maintaining a count of errors in the named object shapes;

a timer for timing an interval taken by the subject to complete naming the object shapes; and a set of predetermined shape-naming error count and interval data against which to compare the shape-naming error count and interval, a shape-naming error count and interval greater than the predetermined shape-naming error count and interval indicative of a possible parietal lobe function deficiency.

11. The testing system recited in claim 10, wherein the objects in the first ordered array all have a substantially analogous shape.

12. The testing system recited in claim 10, wherein the objects in the first ordered array all comprise squares.

13. The testing system recited in claim 10, wherein the objects in the second ordered array all have a substantially analogous color.

14. The testing system recited in claim 10, wherein the first ordered array displaying means comprises a card having indicia thereon representative of the first ordered array of objects, and the second ordered array displaying means comprises a card having indicia thereon representative of the second ordered array of objects.

15. The testing system recited in claim 10, further comprising:

means for displaying to the subject a third ordered array of objects having a variety of shapes and a variety of colors;

means for maintaining a count of errors in the named object colors and shapes;

a timer for timing an interval taken by the subject to complete naming the object colors and shapes; and a set of predetermined color- and shape-naming error count and interval data against which to compare the color- and shape-naming error count and interval, a color- and shape-naming error count and interval greater than the predetermined color- and shape-naming error count and interval indicative of a possible parietal lobe function deficiency.

16. The testing system recited in claim 10, further comprising means for displaying to the subject a practice ordered array of objects having a variety of colors.

17. The testing system recited in claim 10, further comprising means for displaying to the subject a practice ordered array of objects having a variety of shapes.

18. A parietal lobe function test delivery and analysis system comprising:

a processor;

a timing device, a display device, and an input device, all in signal communication with the processor;

a database accessible by the processor containing a set of predetermined standard data;

software means resident on the processor adapted to:

effect a display to a subject on the display device a first ordered array of objects having a variety of colors, each object having a unitary color;

receive from an examiner via the input device a count of errors in the named object colors;

access the timer for timing an interval taken by the subject to complete naming the object colors; for a set access the database for a set of predetermined color-naming error count and interval data;

making a first comparison of the color-naming error count and interval with the predetermined color-naming error count and interval data, a color-naming error count and interval greater than the predetermined color-naming error count and interval indicative of a possible parietal lobe function deficiency;

effect a display to the subject on the display device a second ordered array of objects having a variety of shapes;

receive from the examiner via the input device a count of errors in the named object shapes;

access the timer for timing an interval taken by the subject to complete naming the object shapes;

access the database for a set of predetermined shape-naming error count and interval data;

making a second comparison of the shape-naming error count and interval against the predetermined shape-naming error count and interval data, a shape-naming error count and interval greater than the predetermined shape-naming error count and interval indicative of a possible parietal lobe function deficiency; and output to the examiner a result of the first and the second comparison.

19. The system recited in claim 18, wherein the objects in the first ordered array all have a substantially analogous color.

20. The system recited in claim 18, wherein the objects in the first ordered array all comprise squares.

21. The system recited in claim 18, wherein the objects in the second ordered array all have a substantially analogous shape.

22. The system recited in claim 18, wherein the display comprises a video monitor.

23. The system recited in claim 18, wherein the software is further adapted to:

effect a display to the subject on the display device a third ordered array of objects having a variety of shapes and a variety of colors;

receive from the examiner via the input device a count of errors in the named object colors and shapes;

access the timer for timing an interval taken by the subject to complete naming the object colors and shapes;

access the database for a set of predetermined color- and shape-naming error count and interval data;

making a third comparison of the color- and shape-naming error count and interval with the predetermined color- and shape-naming error count and interval, a color- and shape-naming error count and interval greater than the predetermined color- and shape-naming error count and interval indicative of a possible parietal lobe function deficiency; and output to the examiner a result of the third comparison.

24. The system recited in claim 18, wherein the software is further adapted to effect a display on the display device to the subject a practice ordered array of objects having a variety of colors, for permitting the subject to practice taking a second portion of the test.

25. The system recited in claim 18, wherein the software is further adapted to effect a display on the display device to the subject a practice ordered array of objects having a variety of shapes, for permitting the subject to practice taking a second portion of the test.

26. An automated parietal lobe function test delivery and analysis system comprising:

a processor;

a timing device, a display device, and an input device, all in signal communication with the processor;

a database accessible by the processor containing a set of predetermined standard data;

software means resident on the processor adapted to:

effect a display to a subject on the display device a first ordered array of objects having a variety of colors, each object having a unitary color;

receive from an examiner via the input device a count of errors in the named object colors;

access the timer for timing an interval taken by the subject to complete naming the object colors; for a set access the database for a set of predetermined color-naming error count and interval data;

making a first comparison of the color-naming error count and interval with the predetermined color-naming error count and interval data, a color-naming error count and interval greater than the predetermined color-naming error count and interval indicative of a possible parietal lobe function deficiency;

effect a display to the subject on the display device a second ordered array of objects having a variety of shapes;

receive from the examiner via the input device a count of errors in the named object shapes;

access the timer for timing an interval taken by the subject to complete naming the object shapes;

access the database for a set of predetermined shape-naming error count and interval data;

making a second comparison of the shape-naming error count and interval against the predetermined shape-naming error count and interval data, a shape-naming error count and interval greater than the predetermined shape-naming error count and interval indicative of a possible parietal lobe function deficiency; and output to the examiner a result of the first and the second comparison.

27. The system recited in claim 26, wherein:

the processor and the database are located at a central site, and the software means is adapted to direct the display-effecting and result-outputting steps at a subject site remote from the central site over a communications network.

28. A method for testing parietal lobe function in a subject, the method comprising the steps of:

displaying to a subject a first ordered array of objects, each object having a feature within a first unitary dimension;

prompting the subject to name the feature of each object of the first array sequentially in order;

displaying to the subject a second ordered array of objects, each object having a feature within a second unitary dimension distinct from the first unitary dimension;

prompting the subject to name the feature of each object of the second array sequentially in order;

displaying to the subject a third ordered array of objects, each object having two features, one feature within each of the first and the second unitary dimension;

prompting the subject to name the features of each object of the third array sequentially in order;

timing an interval taken by the subject to complete naming the third array object features; and comparing the interval with a predetermined interval, an interval greater than the predetermined interval indicative of a possible parietal lobe function deficiency.

29. The method recited in claim 28, wherein:

the displaying and prompting steps are performed at a subject site remote from a central site over a communications network; and the comparing step is performed at the central site.

30. The method recited in claim 29, further comprising the step of storing interval and demographic data on the subject at the central site.

31. A computer-readable medium having stored thereon a software program for testing parietal lobe function in a subject, the software program comprising:
   a code segment for displaying to a subject a first ordered array of objects having a variety of colors, each object having a unitary color;
   a code segment for prompting the subject to name the object colors sequentially in order;
   a code segment for comparing the named object colors with the correct object colors;
   a code segment for maintaining a count of errors in the named object colors;
   a code segment for timing an interval taken by the subject to complete naming the object colors;
   a code segment for comparing the color-naming error count and interval with a predetermined color-naming error count and interval, a color-naming error count and interval greater than the predetermined color-naming error count and interval indicative of a possible parietal lobe function deficiency;
   a code segment for displaying to the subject a second ordered array of objects having a variety of shapes;
   a code segment for prompting the subject to name the object shapes sequentially in order;
   a code segment for comparing the named object shapes with the correct object shapes;
   a code segment for maintaining a count of errors in the named object shapes;
   a code segment for timing an interval taken by the subject to complete naming the object shapes; and
   a code segment for comparing the shape-naming error count and interval with a predetermined shape-naming error count and interval, a shape-naming error count and interval greater than the predetermined shape-naming error count and interval indicative of a possible parietal lobe function deficiency.

* * * * *